United States Patent [19]
Nishikawa et al.

[11] Patent Number: 5,648,228
[45] Date of Patent: Jul. 15, 1997

[54] MEASURING ACTIVITY TOWARD PRODUCTION OF ACTIVATED BLOOD COAGULATION FACTOR XII, PLASMA KALLIKREIN OR BRADYKININ USING RECONSTITUTED KALLIKREIN-KININ SYSTEM

[75] Inventors: Katsumi Nishikawa; Hitoshi Kawakubo, both of Katoh-gun, Japan

[73] Assignee: Nippon Zoki Pharmaceutical Co., Ltd., Osaka, Japan

[21] Appl. No.: 284,972

[22] Filed: Aug. 4, 1994

[30] Foreign Application Priority Data

Aug. 6, 1993 [JP] Japan ................... 5-215178

[51] Int. Cl.$^6$ ............... C12Q 1/56; G01N 33/86
[52] U.S. Cl. ............ 435/13; 435/212; 435/214; 436/69
[58] Field of Search ............... 435/13, 23, 24, 435/184, 212, 214, 217; 436/69

[56] References Cited

U.S. PATENT DOCUMENTS

| | | | |
|---|---|---|---|
| 4,335,203 | 6/1982 | Lasser | 435/23 |
| 4,598,043 | 7/1986 | Svendsen | 435/13 |
| 4,882,272 | 11/1989 | Scott | 435/13 |
| 4,985,254 | 1/1991 | Konishi et al. | 424/520 |
| 4,985,354 | 1/1991 | Toyomari | 435/13 |
| 5,013,558 | 5/1991 | Konishi | 424/520 |
| 5,057,324 | 10/1991 | Shibayama | 424/520 |

FOREIGN PATENT DOCUMENTS

| | | |
|---|---|---|
| 0 341 209 A2 | 11/1989 | European Pat. Off. . |
| 53-101515 | 9/1978 | Japan . |
| 57-77697 | 5/1982 | Japan . |
| 58-35117 | 3/1983 | Japan . |
| 697351 | 9/1953 | United Kingdom . |

OTHER PUBLICATIONS

Kaplan, A., "Assessment of Hageman Factor Activation in Human Plasma: Quantification of Activated Hageman Factor-C1 Inactivator Complexes by an Enzyme-Linked Differential Antibody Immunosorbent Assay" *Blood*, vol. 66, No. 3 (Sep.) 1985, pp. 636-641.

Gillmore, M.J., A Direct Chromogenic Peptide Substrate Assay for Hageman Factor (FXII), *J. of Fibrinolysis*, 1(2), 1987, pp. 123-127.

Dumenco, L, Inhibition of the activation of Hageman factor (factor XII) by platelet factor 4, *J. Lab. Clin. Med.*, 112(3), 1988, pp. 394-400.

*Primary Examiner*—Ralph Gitomer
*Attorney, Agent, or Firm*—Fisher, Christen & Sabol

[57] ABSTRACT

The present invention provides a method for measuring the activity of tested substances utilizing a reconstituted plasma kallikrein-kinin system. A series of enzymatic reactions is started wherein an activation of a blood coagulation factor XII is an initiating reaction. The series of reactions is started in the presence of the tested substance in the reconstituted plasma kallikrein-kinin system. Then, the series of reactions is stopped and the physiologically active substance produced in the reaction series is quantitatively determined. In the activity measuring method of the present invention, the real activity (a promoting or inhibiting ability) of the tested substance against the production of the produced physiologically active substance can be easily, simply, quickly and precisely measured. In the reconstituted plasma kallikrein-kinin reaction system the contaminating other factors are substantially removed. Accordingly, the method of measuring the activity in accordance with the present invention is a very advantageous means for ascertaining action which is useful for adjusting the bioregulations in, for example, the plasma kallikrein-kinin system, the blood clotting system, the fibrinolysis system, etc. It may also be used for developing or screening drugs which are related to the systems.

20 Claims, 3 Drawing Sheets

MEASURING ACTIVITY TOWARD PRODUCTION OF ACTIVATED BLOOD COAGULATION FACTOR XII, PLASMA KALLIKREIN OR BRADYKININ USING RECONSTITUTED KALLIKREIN-KININ SYSTEM

FIELD OF THE INVENTION

The present invention relates to a method for measuring an activity of a tested substance towards the production of a physiologically active substance produced in a reconstituted plasma kallikrein-kinin system. More particularly, it relates to a method of measuring a physiologically active substance produced in said reaction system, such as a blood coagulation factor XII in an active form, plasma kallikrein or bradykinin, utilizing a reconstituted system comprising the components of a plasma kallikrein-kinin system.

BACKGROUND OF THE INVENTION

Kallikrein is a protease which is widely distributed in plasma and tissues of various animals including human beings. An enzymatic system known as the kallikrein-kinin system acts in vivo. It has a close relationship with various other enzymatic reaction systems such as a renin-angiotensin system, a blood clotting system, a fibrinolysis system, a complement system as well as catecholamine and arachidonic acid cascade mainly related to prostaglandins, leukotrienes and thromboxanes. Accordingly, the kallikrein-kinin system is closely associated with blood pressure regulating action and blood clotting-fibrinolysis-complement system action. Bioregulation and an improving action for peripheral circulation by various physiologically active substances produced by an arachidonic acid cascade are also related to the kallikrein-kinin system. The kallikrein-kinin system plays an important role in the regulation of functions in vivo.

Kinins, such as bradykinin, are produced in the kallikrein-kinin system. They exhibit various physiological actions such as a decrease in blood pressure due to dilation of peripheral blood vessels, promotion of permeability of blood vessels, contraction or relaxation of smooth muscle, induction of pain, induction of inflammation, migration of leucocytes, liberation of catecholamine from the adrenal cortex, etc. Kinins are also known as mediators in acute inflammations including allergic reactions whereby their existence in vivo has a profound significance.

With respect to this plasma kallikrein-kinin system, it has been believed that a blood coagulation factor XII (a Hageman factor, hereinafter abbreviated as FXII) is activated in vivo by injury and invasive stimulation to tissues whereby a series of enzymatic reaction systems results. Thus, as shown in FIG. 1, the activated blood coagulation factor XII or "Activated FXII" (hereinafter, abbreviated as FXIIa) acts on the plasma prekallikrein which exists in the same plasma to convert it to a plasma kallikrein which is an enzyme in an activated form. Then the plasma kallikrein acts on a high-molecular-weight kininogen (hereinafter abbreviated as an HK) to liberate bradykinin.

Kinins such as bradykinin which are liberated by the enzymatic reaction of the kallikrein-kinin system exhibit various physiological actions as mentioned already. Accordingly, substances which inhibit the action of bradykinin or substances which inhibit the production of bradykinin by interfering with the reactions in the plasma kallikrein-kinin system may be useful as antiinflammatory, analgesic and antiallergic agents.

Further, FXIIa is an important factor in the initiating stage of the intrinsic blood clotting system and the fibrolysis system. Thus, substances which affect the production of FXIIa may be useful as drugs in the areas of blood clotting and fibrinolysis.

Therefore, establishment of a method for measuring the degree to which substances or compounds or components inhibit or promote the reactions in the plasma kallikrein-kinin system in a simple, easy, quick and precise manner is a very important means for ascertaining the action which helps regulation of the above-mentioned bioregulation systems. It is also useful for developing drugs for regulating or controlling the bioregulation systems.

When screenings or the like of drugs using the plasma kallikrein-kinin system are carried out in vitrO, activation of FXII by an invasive stimulation to tissues and injury such as an intravital reaction cannot be conducted. A substance which activates the FXII may be added to an isolated plasma to carry out a reaction which induces a plasma kallikrein-kinin system reaction in vitro.

However, the plasma of animals contain various components in addition to the above-mentioned components. For example, components which have an effect (such as an inhibition or a promotion) on the plasma kallikrein-kinin reaction system and other unknown factors are contained in animal plasma. Accordingly, measuring the activity of the test substance towards the production of the physiologically active substances using animal plasma per se to screen drugs or the like is complicated. The various factors containing unknown components which are in the animal plasma per se may affect the plasma kallikrein-kinin reaction system. Consequently, controlling the reaction system is highly technical and complex when animal plasma per se is used as a source of reactants.

The present invention provides a method for measuring the physiological action of the tested substance in an easy, simple, prompt and precise manner. Factors containing unknown components which may affect the plasma kallikrein-kinin reaction system are eliminated by the use of a reconstituted plasma kallikrein-kinin reaction system. The drug screening reactions may be carried out in vitro in the reconstituted plasma kallikrein-kinin reaction system. The reconstituted plasma kallikrein-kinin system may be obtained by combining components isolated from the plasma kallikrein-kinin system.

SUMMARY OF THE INVENTION

The present invention provides an in vitro method of measuring the activity of a test substance with respect to inhibiting or promoting the production of a physiologically active substance or component involved in the plasma kallikrein-kinin reaction system. Physiologically active substances or components of the reaction system include the blood coagulation factor XII in active form (FXIIa), plasma kallikrein, and bradykinin. The tested substance's ability to inhibit or promote the production of the physiologically active substance, such as FXIIa, is measured in a simple, convenient, prompt and precise manner.

Conducting the reaction in a reconstituted plasma kallikrein-kinin reaction system avoids complications associated with the use of plasma per se as a source of the physiologically active substances such as bradykinin. The reconstituted plasma kallilcrein-kinin reaction system may be obtained by combining the blood coagulation factor XII (FXII), and plasma prekallikrein, and preferably high molecular weight kininogen (HK), each being substantially purified. Each component of the reconstituted plasma kallikrein-kinin reaction system may be separated or purified from plasma or manufactured using genetic engineering techniques.

The measuring method may be used to screen tested substances or compounds for usefulness as pharmaceuticals or drugs for controlling blood clotting, blood pressure, and fibrinolysis. Screening of tested substances for use as anti-inflammatory drugs, analgesics, and antiallergic drugs may also be performed.

To measure the activity of a test substance in accordance with the method of the present invention, a series of enzymatic reactions is initiated. Activation of the blood coagulation factor XII is an initiating reaction for the series of enzymatic reactions. Initiation of the series of reactions is performed in the presence of the test substance or compound. Initiation may be achieved by admixing a blood coagulation factor XII activator with a reconstituted plasma kallikrein-kinin reaction system in the presence of the test substance. Then, the reaction is stopped and the physiologically active substance (such as bradyldnin, FXIIa, or plasma kallikrein) produced in the above reaction is quantitatively determined. The amount of physiologically active substance produced relative to the amount produced in a control sample which does not contain the tested substance or which contains a different test substance may be used to indicate the relative activity of the tested substance.

DETAILED DESCRIPTION OF THE INVENTION

Figure 1:
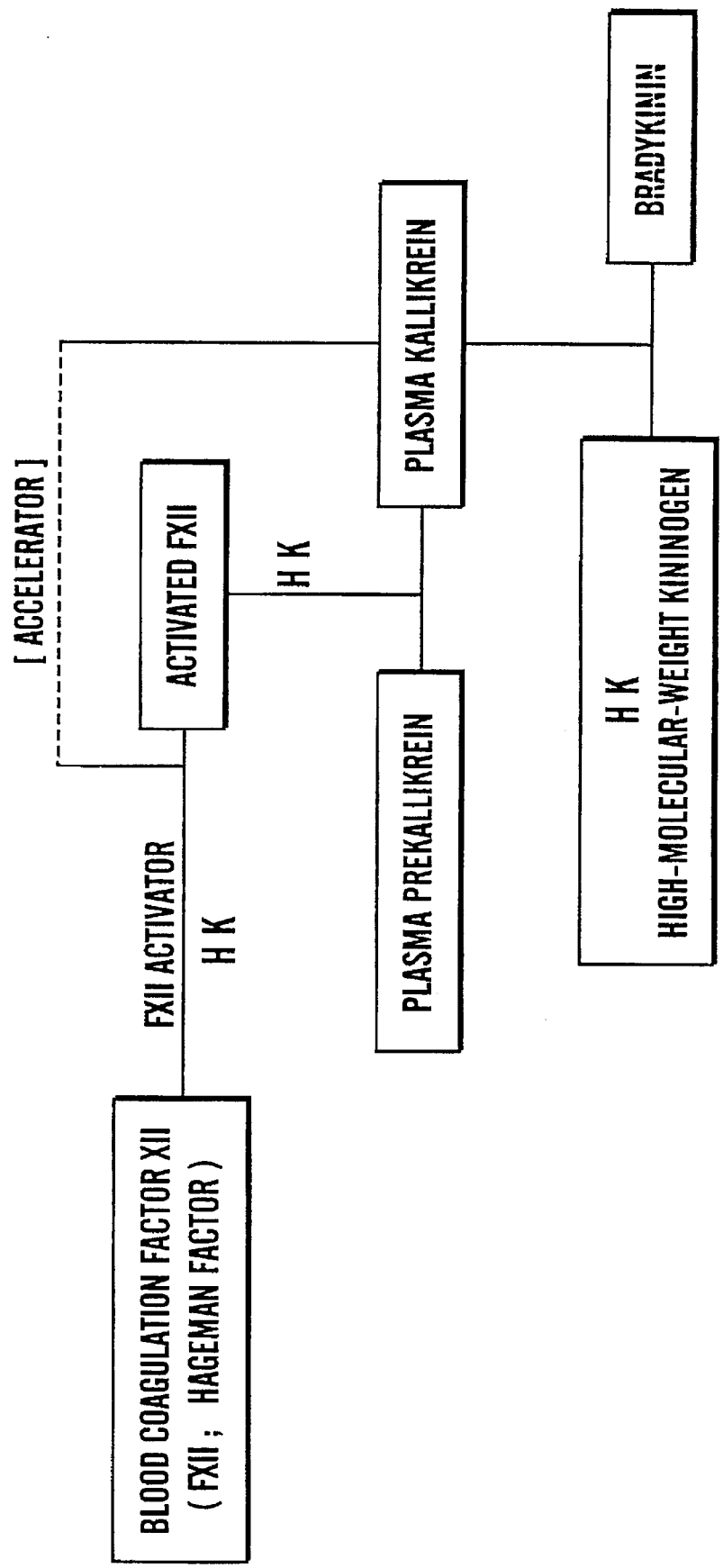
FIG. 1 is a schematic diagram illustrating a series of enzymatic reactions of the plasma kallikrein-kinin reaction system.

In the present invention, a substance is tested for its ability to inhibit or promote the production of a physiologically active substance or component involved in the plasma kallikrein-kinin reaction system. The physiologically active substance may be plasma kallikrein, bradykinin, or the blood coagulation factor XII in active form (FXIIa). The test may be conducted in vitro by starting the activation of a series of enzymatic reactions in the presence of the test substance in a reconstituted plasma kallikrein-kinin system. The initiating reaction of the series of enzymatic reactions is the activation of the blood coagulation factor XII (FXII) to produce the blood coagulation factor in an activated state (FXIIa).

The measuring method may be conducted by admixing a blood coagulation factor XII activator with a reconstituted plasma kallikrein-kinin system comprising a blood coagulation factor II (FXII), plasma prekallikrein, and preferably high molecular weight kininogen (HK), to initiate activation of the FXII in the presence of the test substance. The reaction is stopped and the amount of physiologically active substance produced in the reaction is quantitatively determined. The amount produced is an indication of the effectiveness or activity of the tested substance in promoting or inhibiting the production of the physiologically active substance in a physiological reaction system involving FXII and plasma prekallikrein. The effect of the tested substances on production of FXIIa, plasma kallikrein, or bradykinin may be used to screen them for usefulness as antiinflammatory, analgesic, and antiallergic drugs and as pharmaceuticals for controlling blood pressure, blood clotting, and fibrinolysis.

With respect to the constituting components in the reconstituted plasma kallikrein-kinin system in the measuring method of the present invention, FXII and plasma prekallikrein can be used when the physiologically active substance to be determined is FXIIa or plasma kallikrein. A preferred reaction system may also be constructed by adding a high molecular weight kininogen (HK) thereto. In the case of the quantitative determination of bradykinin, it is preferred to utilize a system which is reconstituted using FXII, plasma prekallikrein and HK. With regard to each of those constituting components, that which is substantially purified may be used. The FXII, plasma prekallikrein, and HK which are utilized in producing the reconstituted plasma kallikrein-kinin reaction systems may each be separated or purified from plasma or manufactured by a means of gene technology. The plasma of any animal may be used as the source of the purified or separated components provided it has a blood clotting system and a plasma kallikrein-kinin system. For example, human plasma and plasma of cattle and experimental animals such as cows, sheep, pigs, horses, goats, monkeys, dogs, cats, rabbits, guinea pigs, hamsters, rats or mice may be utilized as sources of the components. Preferably, human plasma is used as the source of the components used in obtaining the reconstituted plasma kallikrein-kinin reaction systems.

With respect to the activating agent for FXII for inducing the activating reaction of the plasma kallikrein-kinin system, any substance may be used provided it activates the FXII. Examples of substances which may be used as an FXII activator are glass, kaolin, celite, collagen, homocystine, sodium urate, cell components such as membranes of platelets and other cells, fibronectin, elaidic acid, quercetin, rutin, sulfated glycolipids, proteoglycan, mucopolysaccharides, sodium stearate, dextran sulfate, amylose sulfate, carrageenin and proteases which activate FXII by a restricted decomposition. They may be used either solely or jointly. The concentration of the FXII activators may be selected in effective concentrations for activating FXII.

In the mixing reaction carried out by adding an FXII activator to a solution comprising a substantially purified FXII, plasma prekallikrein and preferably HK, the reaction temperature may be suitably adjusted so as to make the reaction easily controllable. For example, the reaction may be carried out at a reaction temperature of 0° C. to 4° C. using an ice water bath. It is preferred that the mixing reaction is carried out at a pH where the plasma kallikrein-kinin system reaction smoothly proceeds, such as from 7.0 to 9.0. In order to adjust to a suitable reaction condition, salts such as sodium chloride, metal ions such as zinc ion and other additives and auxiliary agents which are commonly used in this art may be added to the reaction system.

The reaction time for the mixing reaction may be adjusted depending upon the concentrations of the above-mentioned FXII, FXII activators, plasma prekallikrein, HK and the tested substance as well as upon the pH of the reaction solution. However, when the produced amount of the physiologically active substance to be quantitatively determined is saturated, it is not possible to correctly evaluate the action of the tested substance. Therefore, it is preferred to set the reaction time so that it is less than the time it takes for production of a saturated amount of the physiologically active substance to be determined. In other words, it is preferred to set the reaction time within a time that a clear positive relationship between the reaction time and the produced physiologically active exists. A reaction time during which there is a subs is preferred for the evaluation.

The method for stopping the production of the physiologically active substance in the above-mentioned mixing reaction may be suitably selected depending upon the physiologically active substance to be determined. Thus, in the case of a quantitative determination of FXIIa for example, it is preferred to use an FXII activation inhibitor (e.g. polybrene) and inhibitors which specifically inhibit the plasma kallikrein, most preferably plasma kallikrein inhibitors which do not substantially affect FXIIa such as SBTI. SBTI (soy bean trypsin inhibitor) is a trypsin inhibitor prepared from soy bean. When the reaction is stopped, the produced FXIIa can be quantitatively determined using an enzymatic activity of FXIIa as a target by applying a substrate to FXIIa.

In the quantitative determination of a plasma kallikrein, it is preferred to use substances which stop the production of plasma kallikrein (e.g., inhibitors which specifically inhibit FXIIa, most preferably, inhibitors which do not substantially affect the plasma kallikrein such as LBTI and CHFI. LBTI is lima bean trypsin inhibitor, a trypsin inhibitor prepared from lima bean. CHFI is corn Hageman fragment inhibitor, a Hageman fragment inhibitor prepared from corn. When the reaction is stopped, the produced plasma kallikrein can be determined using an enzymatic activity of the plasma kallikrein as a target by utilizing a substrate to the plasma kallikrein.

When bradykinin is quantitatively determined as a produced physiologically active substance, it is possible to use a substance which stops the production of bradykinin such as the above-mentioned inhibitors to FXIIa and plasma kallikrein having an action of liberating bradykinin by a restricted decomposition of HK, as well as organic solvents such as acetone and ethanol, or acids such as hydrochloric acid and perchloric acid.

The concentration of the substances which are used for stopping the production of the physiologically active substances may be suitably selected so that the quantitative determination of each of the physiologically active substances is not substantially affected.

Quantitative determination of the produced physiologically active substance may be carried out by conventional measuring methods. For example, with respect to a method of measuring the produced amount of FXIIa, a method wherein a substrate to FXIIa is used utilizing the enzymatic activity of FXIIa may be applied. Known methods using a natural substrate such as plasma prekallikrein, FXI or plasmin, a coloring synthetic substrate such as D-Pro-Phe-Arg-pNA or D-Leu-Gly-Arg-pNA or a fluorescent synthetic substrate such as Boc-Glu(OBz)-Gly-Arg-MCA or Boc-Gln-Gly-Arg-MCA provide simple and convenient ways for the quantitative determination of FXIIa produced.

In the quantitative determination of the produced plasma kallikrein, known methods in which a natural substrate such as FXII or HK, a coloring synthetic substrate such as D-Pro-Phe-Arg-pNA or Bz-Pro-Phe-Arg-pNA or a fluorescent synthetic substrate such as Z-Phe-Arg-MCA may be used as well.

Besides the above-mentioned measuring methods using the substrates, immunological measuring methods such as a radioimmunoassay (RIA) or an enzyme immunoassay (EIA), quantitative determination using chromatography, etc., may be used too.

With respect to the method for quantitative determination of the produced bradykinin, commonly-used means such as bioassay, RIA, EIA, etc. may be used. Any method may be chosen depending upon the conditions such as the number of the tested substances, devices in the measuring facilities, preciseness requested for the measurement, etc.

The present invention is further illustrated by way of the following examples:

EXAMPLE 1

Dextran sulfate was added to make the final concentration 5 micrograms/ml to a solution comprising 6 nM of FXII, 35 nM of plasma prekallikrein, 10 nM of HK, a certain amount of the tested substance and 25 mM of a Tris hydrochloride buffer (pH: 8) containing Triton X-100, BSA and 100 mM of NaCl. The mixture was incubated in ice water and LBTI was added to the reaction solution to make the final concentration 20 mg/ml. The reaction solution was incubated at 30° C. for 30 minutes in a Tris hydrochloride buffer (pH: 8) together with 1 mM of D-Pro-Phe-Arg-pNA (a synthetic substrate). The reaction was stopped by adding citric acid to the reaction mixture. The mixture was centrifuged at 3,000 rpm for ten minutes and the absorbance (which corresponds to the amount of plasma kallikrein produced) of the resulting supernatant liquid at 405 nm was measured. The absorbance as a function of incubation time or reaction time in the ice bath is shown in FIG. 2.

EXAMPLE 2

The same operations as in Example 1 were carried out with the exception that 0.6 nM of FXII was used instead of 6 nM. The absorbance measured at 405 nm as a function of incubation time or reaction time in the ice bath is shown in FIG. 2.

Figure 2:
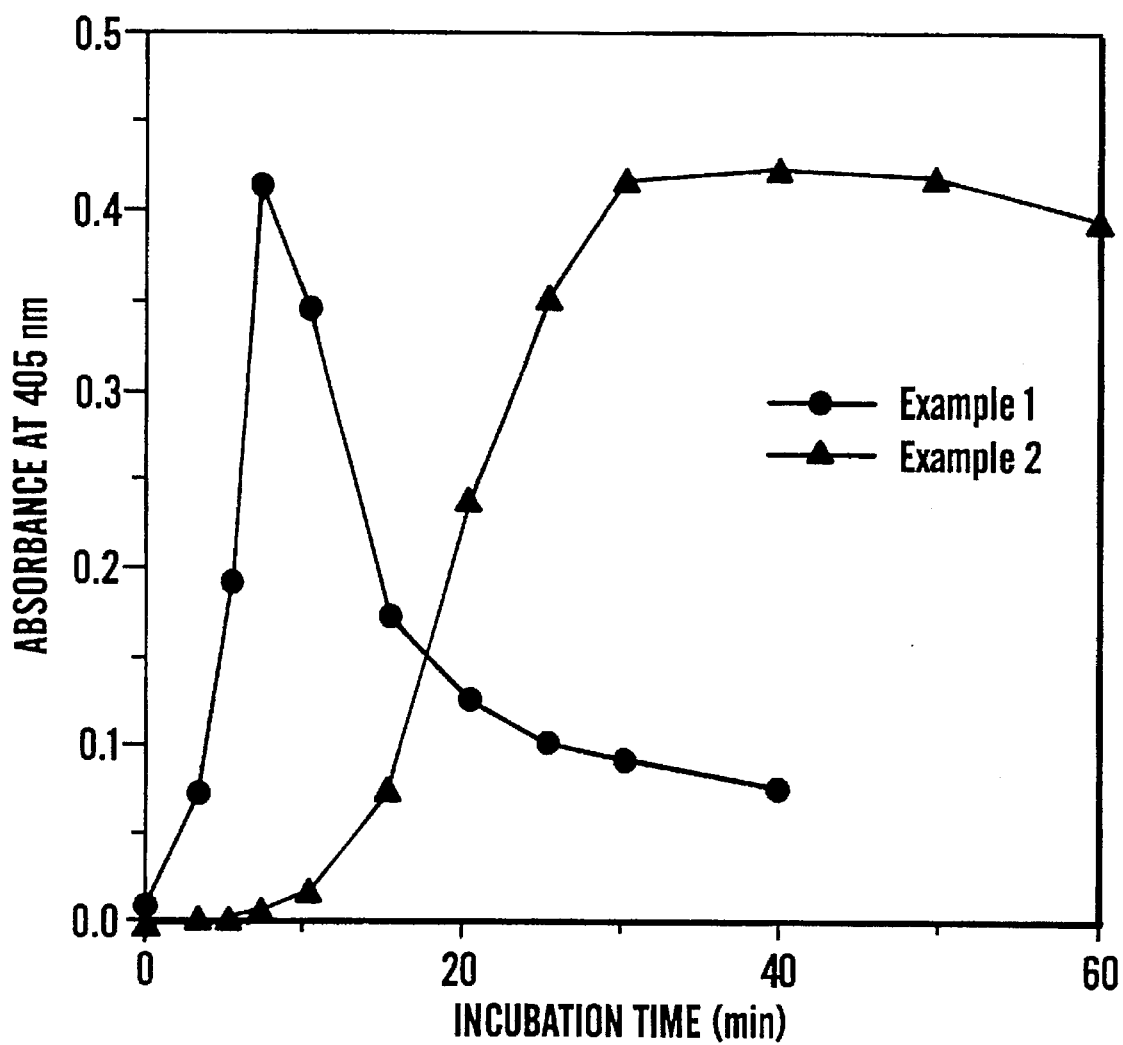
FIG. 2 is a graph showing the changes in the absorbance as a function of incubation time in the measuring method of the present invention wherein the absorbance corresponds to the amount of plasma kallikrein produced in Examples 1 and 2.

FIG. 2 shows the changes in the absorbances when the incubating time was changed in Example 1 (●) and in Example 2 (▲). In FIG. 2, the abscissa shows the incubating time (minutes) while the ordinate shows the absorbances at 405 nm. In the case of Example 1, kallikrein was produced in an almost linearly increasing amount with lapse of time until the incubating time reached about seven minutes. Its production arrived at the saturated point after about seven minutes. Accordingly, it is preferred that the incubating time or reaction time is set to be between 0 and 7 minutes. In the case of Example 2, the time required for saturation of the kallikrein production can be elongated to 30 minutes. In addition, the amount of the plasma prekallikrein in Example 2 was the same as that in Example 1. Therefore, the intensity of the absorbance which is finally measurable was 0.4 and was the same as that in Example 1.

When animal plasma is used instead of the reconstituted plasma kallikrein-kinin reaction system of the present invention, the animal plasma is ten times diluted for decreasing the amount of the FXII to one-tenth. At the same time, the amount of the plasma prekallikrein is decreased to one-tenth as well. Therefore, the intensity of the absorbance to be measured for plasma kallikrein at the end is as low as one-tenth whereby the measurement is almost impossible.

Figure 3:
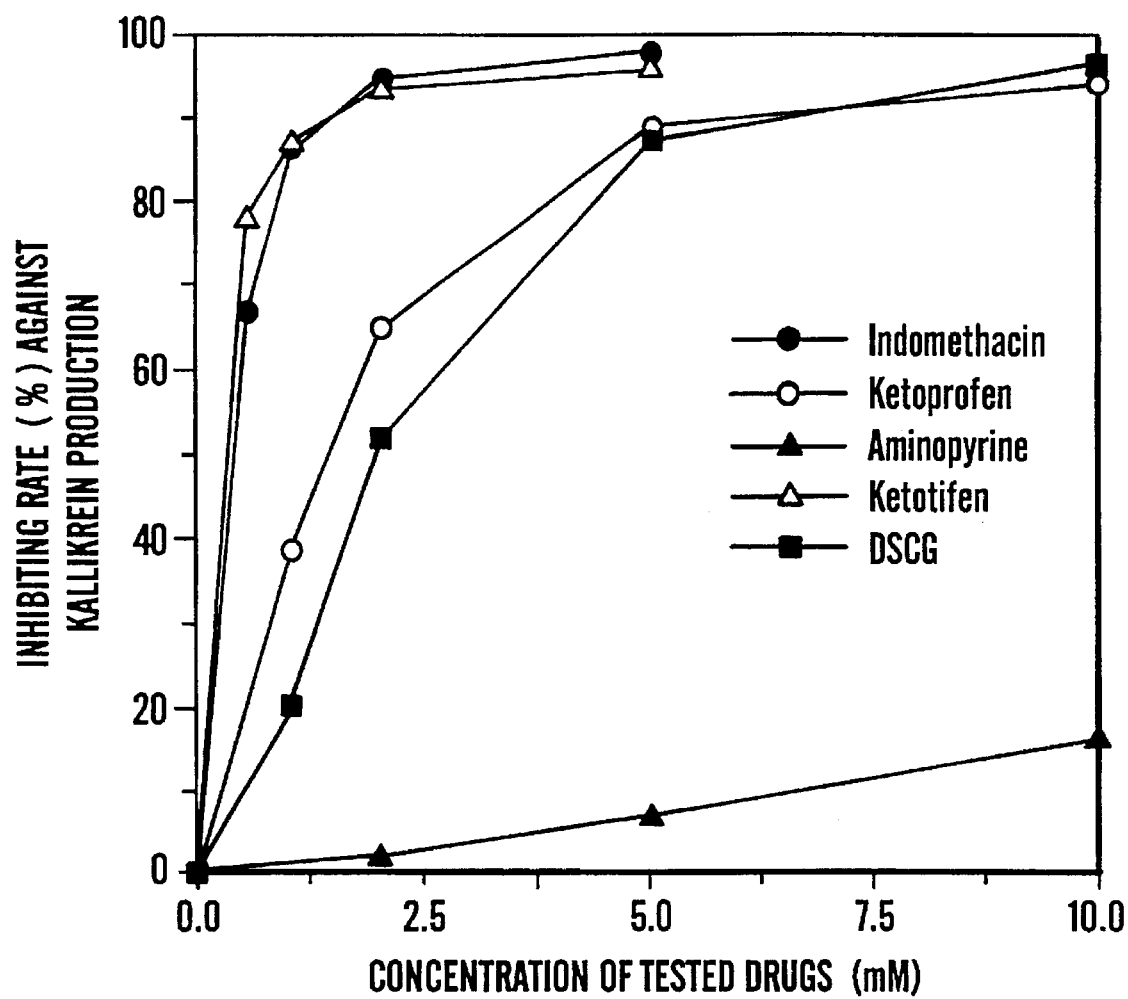
FIG. 3 is a graph showing the results in the measurement of the inhibiting activity of five tested drugs towards the production of plasma kallikrein using the activity measuring method of the present invention in accordance with Examples 1 and 2.

FIG. 3 shows the results of the measurement of the activity for inhibiting the plasma kallikrein production for five drugs (indomethacin, ketoprofen, aminopyrine, ketotifen and disodium cromoglycate which is abbrevated as DSCG) which are used as analgesic or antiallergic drugs utilizing the method of measuring the activity according to the present invention in accordance with Examples 1 and 2. In FIG. 3, the abscissa is the concentrations (mM) of the tested drugs while the ordinate is the inhibiting rate (%) against the production of kallikrein.

The method of measuring the activity according to the present invention utilizing the reconstituted plasma kallikrein-kinin system provides a reaction system in which the contaminating other factors are substantially removed. Therefore, it is not necessary to regulate the reaction to compensate for the factors which may affect the enzymatic reaction system of the plasma kallikrein-kinin system and unknown components therein. Accordingly, the real activity (a promoting or inhibiting ability) of the tested substance towards the production of the physiologically active substance produced in the plasma kallikrein-kinin system can be measured in an easy, convenient prompt and precise manner.

In the measuring method of the present invention, each substantially purified component is used in place of the animal plasma. The advantages of using the substantially purified components to form a reconstituted plasma kallikrein-kinin reaction system compared to using a conventional animal plasma are:

1. The amount of each of the constituting components can be freely adjusted and, accordingly, reaction time, reaction temperature, absorbance, etc. in the reaction system can be suitably chosen depending upon the numbers of the tested substances and the required precision.
2. The influence of the endogenous inhibitors such as $\alpha_2$ macroglobulin and C1-inhibitor, and kininase being present in the animal plasma can be substantially neglected. In addition, it is not necessary to take the factors which may affect the reaction and unknown substances in the animal plasma into consideration. Consequently, the real activity of the tested substance towards the production of the physiologically active substance produced in the plasma kallikrein-kinin system can be measured precisely. To be more specific, there is an advantage that, for example, there is no need of using a kininase inhibitor in the measurement of the action of the tested substance towards the production of bradykinin.
3. The scattering in the reactions due to the lack of uniformity in the components of animal plasma can be prevented whereby an increase in the precision of the measurement results.

In the quantitative determination of the produced physiologically active substances in the measuring method of the present invention, various methods such as a method of measuring the inhibiting ability against the production of FXIIa, a method of measuring the inhibiting ability against the production of plasma kallikrein, and a method of measuring the inhibiting ability against the production of bradykinin can be suitably selected. Accordingly, the degree of freedom in the measurement and the applicable range are broad.

Furthermore, in the method for measuring the activity of the present invention, a reconstituted system wherein each component is substantially purified is used and the contaminating other factors are removed makes it possible to screen drugs or compounds having activity towards the production (a promoting or an inhibiting activity for the production) of various physiologically active substances in the plasma kallikrein-kinin system from several viewpoints. The screening of drugs or compounds may be based upon a clear and specific action mechanism. Accordingly, the present invention achieves a significant beneficial effect on the development of new drugs for various diseases.

What is claimed is:

1. A method of measuring the activity of a test substance toward the production of blood coagulation factor XII in at active form, plasma kallikrein or bradykinin comprising initiating a series of enzymatic reactions wherein activation of a blood coagulation factor XII which is in an inactive form is an initiating reaction, the series of reactions being initiated in the presence of the test substance in a reconstituted plasma kallikrein-kinin system wherein $\alpha_2$ macroglobulin, C-1 inhibitor, and kininase are substantially absent, said reconstituted plasma kallikrein-kinin system consisting essentially of: (a) a blood coagulation factor XII which is in an inactive form, (b) plasma prekallikrein, and (c) a high molecular weight:kininogen, then stopping said series of reactions, and quantitatively determining the a mount of blood coagulation factor XII in an active form, plasma kallikrein or bradykinin produced in said series of enzymatic reactions as a measure of the activity of the test substance.

2. A method as claimed in claim 1 wherein said series of enzymatic reactions is initiated with at least one activator selected from the group consisting of glass, kaolin, celite, collagen, homocystine, sodium urate, cell components of blood platelets, fibronectin, elaidic acid, quercetin, rutin, sulfated glycolipids, proteoglycan, mucopolysaccharides, sodium stearate, dextran sulfate, amylose sulfate, carrageenin and proteases which activate the blood coagulation factor XII by a restricted decomposition.

3. A method as claimed in claim 1 wherein the test substance is a blood pressure controlling agent, an antiinflammatory agent, an antiallergic agent, or an analgesic.

4. A method as claimed in claim 1 wherein the test substance is a drug which is related to the blood clotting system or the fibrinolysis system.

5. A method as claimed in claim 1 wherein said reconstituted system is obtained by combining blood coagulation factor XII and plasma prekallikrein, each being substantially purified.

6. A method according to claim 1 wherein the production of blood coagulation factor XII in an active form, plasma kallikrein or bradykinin is stopped before the amount produced is a saturated amount.

7. A method according to claim 6 wherein the activity of the test substance toward the production of blood coagulation factor XII in an active form is measured by determining the amount of blood coagulation factor XII in an active form which is produced in said series of enzymatic reactions.

8. A method as claimed in claim 7 wherein the amount of blood coagulation factor XII in an active form which is produced in said series of reactions is quantitatively determined by incubation with a substrate to the blood coagulation factor XII in an active form.

9. A method as claimed in claim 8 wherein said substrate is a synthetic substrate to the blood coagulation factor XII in an active form.

10. A method as claimed in claim 7 wherein said reaction is stopped by polybrene and soybean trypsin inhibitor.

11. A method according to claim 6 wherein the activity of the test substance toward the production of plasma kallikrein is measured by determining the amount of plasma kallikrein produced in said series of enzymatic reactions.

12. A method as claimed in claim 11 wherein the amount of plasma kallikrein which is produced in said series of reactions is quantitatively determined by incubation with a substrate to the plasma kallikrein.

13. A method as claimed in claim 12 wherein said substrate is a synthetic substrate to the plasma kallikrein.

14. A method as claimed in claim 11 wherein said reaction is stopped by lima bean trypsin inhibitor or corn Hageman fragment inhibitor.

15. A method according to claim 6 wherein the activity of the test substance toward the production of bradykinin is measured by determining the amount of bradykinin produced in said series of enzymatic reactions.

16. A method as claimed in claim 15 wherein the amount of bradykinin which is produced in said series of reactions is quantitatively determined by an immunological measuring method.

17. A method as claimed in claim 15 wherein said reaction is stopped by an organic solvent or an acid which can stop the production of bradykinin.

18. A method as claimed in claim 6 wherein the series of enzymatic reactions is stopped within a period of time during which the amount of blood coagulation factor XII in an active form, plasma kallikrein or bradykinin which is produced is substantially linear with respect to reaction time.

19. A method of measuring the activity of a test substance toward the production of blood coagulation factor XII in an active form, plasma kallikrein or bradykinin comprising initiating a series of enzymatic reactions wherein activation of a blood coagulation factor XII which is in inactive form is an in initiating reaction, the series of reactions being initiated in the presence of the test substance in a reconstituted plasma kallikrein-kinin system wherein $\alpha_2$ macroglobulin , C-1 inhibitor, and kininase are substantially absent, said reconstituted plasma kallikrein-kinin system being obtained by combining substantially purified blood coagulation factor XII which is in an active form with substantially purified plasma prekallikrein, then stopping said reactions, and quantitatively determining the amount of blood coagulation factor XII in an active form, plasma kallikrein, or bradykinin produced in said series of enzymatic reactions as a measure of the activity of the test substance.

20. A method as claimed in claim 14 wherein said reconstituted plasma kallikrein-kinin system is obtained by combining substantially purified blood coagulation factor XII which is in inactive form with substantially purified plasma prekallikrein and substantially purified high molecular weight kininogen, and wherein each of the substantially purified components are separated or purified from plasma.

* * * * *